(12) United States Patent
Suzuki et al.

(10) Patent No.: US 11,219,663 B2
(45) Date of Patent: Jan. 11, 2022

(54) COMPOSITION CONTAINING CYCLIC DIPEPTIDE AND SWEETENING AGENT

(71) Applicant: SUNTORY HOLDINGS LIMITED, Osaka (JP)

(72) Inventors: Toshihide Suzuki, Kyoto (JP); Natsumi Hiraki, Kyoto (JP)

(73) Assignee: SUNTORY HOLDINGS LIMITED, Osaka (JP)

(*) Notice: Subject to any disclaimer, the term of this patent is extended or adjusted under 35 U.S.C. 154(b) by 691 days.

(21) Appl. No.: 15/746,834

(22) PCT Filed: Jul. 26, 2016

(86) PCT No.: PCT/JP2016/071817
§ 371 (c)(1),
(2) Date: Jan. 23, 2018

(87) PCT Pub. No.: WO2017/018404
PCT Pub. Date: Feb. 2, 2017

(65) Prior Publication Data
US 2018/0214508 A1 Aug. 2, 2018

(30) Foreign Application Priority Data
Jul. 27, 2015 (JP) .................. JP2015-147652

(51) Int. Cl.
| A61K 38/12 | (2006.01) |
| A61K 31/7004 | (2006.01) |
| A61K 31/704 | (2006.01) |
| A61K 38/00 | (2006.01) |
| A61K 31/216 | (2006.01) |
| A61K 31/54 | (2006.01) |
| A61K 31/7016 | (2006.01) |
| A61K 38/05 | (2006.01) |

(52) U.S. Cl.
CPC ........... *A61K 38/12* (2013.01); *A61K 31/216* (2013.01); *A61K 31/54* (2013.01); *A61K 31/7004* (2013.01); *A61K 31/704* (2013.01); *A61K 31/7016* (2013.01); *A61K 38/00* (2013.01); *A61K 38/05* (2013.01)

(58) Field of Classification Search
None
See application file for complete search history.

(56) References Cited

U.S. PATENT DOCUMENTS

| 5,034,609 | A | 7/1991 | Satake et al. |
| 2003/0060428 | A1 | 3/2003 | Hermansen et al. |
| 2007/0116840 | A1 | 5/2007 | Prakash et al. |
| 2007/0286938 | A1 | 12/2007 | Saiki et al. |
| 2008/0107787 | A1 | 5/2008 | Prakash et al. |
| 2012/0283178 | A1 | 11/2012 | Tsuruoka et al. |
| 2014/0243514 | A1* | 8/2014 | Brower, III ............... C07H 1/08 536/18.1 |
| 2016/0106130 | A1 | 4/2016 | Yamamoto et al. |
| 2017/0129919 | A1* | 5/2017 | Suzuki ..................... A23G 1/44 |

FOREIGN PATENT DOCUMENTS

| AU | 2014386720 A1 | 1/2016 |
| CN | 101461441 A | 6/2009 |
| CN | 103974628 A | 8/2014 |
| CN | 104817615 A | 8/2015 |
| EA | 201390347 A1 | 7/2013 |
| EP | 1698703 A1 | 9/2006 |
| EP | 2676556 A1 | 12/2013 |
| EP | 3158996 A1 | 4/2017 |
| EP | 3158997 A1 | 4/2017 |
| JP | 2003-521528 A | 7/2003 |
| JP | 2003-252896 A | 9/2003 |
| JP | 2005-206528 A | 8/2005 |
| JP | 2009-517038 A | 4/2009 |
| JP | 2010-166911 A | 8/2010 |
| JP | 2011-136916 A | 7/2011 |
| JP | 2012-517214 A | 8/2012 |
| JP | 2012-517998 A | 8/2012 |
| JP | 5456876 B1 | 4/2014 |
| JP | 2014-139224 A | 7/2014 |
| JP | 5690028 B1 | 3/2015 |
| WO | 2006/116814 A1 | 11/2006 |
| WO | 2011-077759 A1 | 6/2011 |
| WO | 2011-077761 A1 | 6/2011 |
| WO | 2012/033789 A2 | 3/2012 |
| WO | 2012/111820 A1 | 8/2012 |
| WO | 2013/176738 A1 | 11/2013 |
| WO | 2014/200000 A1 | 12/2014 |
| WO | 2015/194070 A1 | 12/2015 |
| WO | 2015/194447 A1 | 12/2015 |
| WO | WO-2015194205 A1 * | 12/2015 ............... C07K 5/06 |

OTHER PUBLICATIONS

Prasad "Bioactive Cyclic Dipeptides," Peptides, 1995, vol. 16, No. 1, pp. 151-164 (Year: 1995).*
Giessen et al. "Rational and combinatorial tailoring of bioactive cyclic dipeptides," Frontiers in Microbiology, 2015, vol. 6, Article 785, pp. 1-11 (Year: 2015).*
Ortiz et al. "Cyclic Dipeptides: Secondary Metabolites Isolated from Different Microorganisms with Diverse Biological Activities," Current Medicinal Chemistry, 2017, 24, 2773-2780 (Year: 2017).*
Medline Plus entry for Blood sugar (downloaded from medlineplus. gov/bloodsugar.html on Oct. 1, 2020) (Year: 2020).*
Ceunen et al. "Steviol Glycosides: Chemical Diversity, Metabolism, and Function," J. Nat. Prod. 2013, 76, 1201-1228 (Year: 2013).*
Brown et al. "Non-Nutritive Sweeteners and their Role in the Gastrointestinal Tract," J Clin Endocrinol Metab. Aug. 2012; 97(8): 2597-2605 (Year: 2012).*

(Continued)

*Primary Examiner* — Christina Bradley
(74) *Attorney, Agent, or Firm* — Westerman, Hattori, Daniels & Adrian, LLP

(57) ABSTRACT

Provided a composition excellent in biological safety and capable of enhancing GLP-1 secretion-accelerating effect due to a sweetening agent. The content ratio of the cyclic dipeptide or a salt thereof and a sweetening agent in a composition is controlled to fall within a specified range. Owing to this, GLP-1 secretion-accelerating effect due to the sweetening agent is enhanced.

11 Claims, 2 Drawing Sheets

(56) References Cited

OTHER PUBLICATIONS

Pepino "Metabolic effects of non-nutritive sweeteners," Physiology & Behavior 152 (2015) 450-455 (Year: 2015).*

Sobolevskaya et al. "Bioactive metabolites of the marine actinobacterium *Streptomyces* sp. KMM 7210," Russian Chemical Bulletin, International Edition, vol. 56, No. 4, p. 838-840, Apr. 2007 (Year: 2007).*

Gondry et al. "Cyclodipeptide synthases are a family of tRNA-dependent peptide bond-forming enzymes," Nature Chemical Biology, 2009, 5(6):414-20 (Year: 2009).*

Healthline Sucrose vs Glucose vs Fructose: What's the difference? downloaded from www.healthline.com/nutrition/sucrose-glucose-fructose on Oct. 2, 2020 (Year: 2020).*

Drugbank entry for Sweetening Agents, Accessopm No. DBCAT000378 downloaded from go.drugbank.com/categories/DBCAT000378 on Oct. 3, 2020 (Year: 2020).*

Requirement for Restriction Election dated Nov. 20, 2018, issued in U.S. Appl. No. 15/740,060. (11 pages).

Manner et al., "The Antinocicpetive Effects of Branched-Chain Amino Acids:Evidence for Their Ability to Potentiate Morphine Analgesia", Pharmacology Biochemistry and Behavior, 1996, vol. 53, No. 2, pp. 449-454; cited in Requirement for Restriction Election dated Nov. 20, 2018. (6 pages).

Sakurada et al., "Antinociceptive Activities of Synthetic Dipeptides in Mice", J. Parm. Pharmacol., 1982, 34, pp. 750-751; cited in in Requirement for Restriction Election dated Nov. 20, 2018. (2 pages).

Ra, K.S. et al., "Hypoglycemic Effects of Cyclo (His-Pro) in Streptozotocin-induced Diabetic Rats", Biotechnology and Bioprocess Engineering, 2012, vol. 17, pp. 176-184; cited in ISR dated Sep. 20, 2016.

Jeppesen, P. B., et al., "Stevioside Acts Directly on Pancreatic beta Cells to Secrete Insulin: Actions Independent of Cyclic Adenosine Monophosphate and Adenosine Triphosphate-Sensitive K+-Channel Activity", Metabolism, Feb. 1, 2000, vol. 49, No. 2, pp. 208-214, XP004631489; cited in EESR dated Apr. 3, 2019.

International Search Report dated Sep. 20, 2016, issued in counterpart International Application No. PCT/JP2016/071817. (14 pages).

Extended (supplementary) European Search Repod dated Apr. 3, 2019, issued in counterpart EP Application No. 16830509.2. (9 pages).

Herman, L. et al., "Angiotensin Converting Enzyme Inhibitors (ACEI)", from https://www.ncbi.nlm.nih.gov/books/NBK431051/ StatPeals Publishing, Nov. 22, 2018, pp. 1-7; cited in U.S. Non-Final Office Action dated Feb. 26, 2019.

Giraldo, E. "Overview of Stroke", from https://www.merckmanuals.com/professional/neurologic-disorders/stroke/overview-of-stro . . . , Feb. 2017, pp. 1-9; cited in US Non-Final Office Action dated Feb. 26, 2019.

Cardiac Disease, from https://www.merckmanuals.com/professional/SearchResults?query=cardiac+disease, pp. 1-18, accessed Jan. 27, 2019; cited in U.S. Non-Final Office Action dated Feb. 26, 2019.

Understanding Heart Failure, from https://my.clevelandclinic.org/health/diseases/17069-heart-failure-understaning-heart-failure, Nov. 9, 2018, pp. 1-10; cited in U.S. Non-Final Office Action dated Feb. 26, 2019.

Causes of Health Failure, from https://www.heart.org/en/health-topics/heart-failure/causes-and-risks-for-heart-failure/causes-of-heart-failure, pp. 1-4, accessed Jan. 27, 2019; cited in U.S. Non-Final Office Action dated Feb. 26, 2019.

MacGill, M., "Everything you need to know about hypertension", from https://www.medicalnewstoday.com/articles/150109.php, Nov. 21, 2018, pp. 1-12; cited in U.S. Non-Final Office Action dated Feb. 26, 2019.

High blood pressure, from https://www.mayoclinic.org/diseases-conditions/high-blood-pressure/symptoms-causes/syc . . . , pp. 1-5, accessed Jan. 27, 2019; cited in U.S. Non-Final Office Action dated Feb. 26, 2019.

Leucine:the muscle maker, from https://www.wellbeing.com.au/body/fitness/leucine-the-muscle-maker.html, Nov. 9, 2010, pp. 1-2; cited in U.S. Non-Final Office Action dated Feb. 26, 2019.

Non-Final Office Action dated Feb. 26, 2019, issued in U.S. Appl. No. 15/740,060. (46 pages).

Prasad et al., "Could Dietary Proteins Serve as Cyclo(His-Pro) Precursors?", Neuropeptides, 1991, pp. 17-21, Longman Group, UK Ltd, UK.

Perrotta, E. et al, "2,6-Diketopeperazines from Amino Acids, from Solution-Phase to Solid-Phase Organic Synthesis", Journal of Combinatorial Chemistry, Jan. 2001, vol. 3, No. 5, pp. 453-460, cited in Extended (supplementary) European Search Report dated Dec. 22, 2016.

Extended (supplementary) European Search Report dated Dec. 22, 2016, issued in counterpart European Application No. 14810329.4. (10 pages).

International Search Report dated Sep. 16, 2014, issued in related International Application No. PCT/JP2014/065388 (U.S. Appl. No. 14/896,953) (2 pages).

Prasad, C., "Bioactive Cyclic Dipeptides", Peptides, 1995, vol. 16, No. 1, pp. 151-164; cited in Japanese Office Action dated May 22, 2018.

Kanzaki, H., "Production of novel bioactive compounds by cyclic dipeptide dehydrogenase", Bioscience and Industry, 2002, vol. 60, No. 7, pp. 26-29 (through p. 454-457); with partial English translation; cited in Japanese Office Action dated May 22, 2018.

Office Action dated May 22, 2018, issued in counterpart Japanese Application No. 2015-522799, with English machine translation. (17 pages).

Office Action dated Apr. 6, 2018, issued in counterpart Russian Application No. 2015155291, with English translation. (10 pages).

Search Report dated Apr. 6, 2018, issued in counterpart Russian Application No. 2015155291, with English translation. (5 pages).

Non-Final Office Action dated Sep. 14, 2018, issued in U.S. Appl. No. 14/896,953 (29 pages).

Davies, John S., "The Cyclization of Peptides and Depsipeptides", Journal of Peptide Science, 2003, 9, pp. 171-501; Cited in U.S. Office Action dated Jul. 25, 2019.

Final Office Action dated Jul. 25, 2019, issued in U.S. Appl. No. 15/740,060 (27 pages).

Extended European Search Report dated Jan. 7, 2019, issued in counterpart International Application No. 16818003.2 (5 pages).

Temizkan, S. et al., "Sucralose enhances GLP-1 release and lowers blood glucose in the presence of carbohydrate in healthy subjects but not in patients with type 2 diabetes", European Journal of Clinical Nutrition, 2015, 69, pp. 162-166; Cited in CN Office Action dated Aug. 28, 2020.

Ripken, Dina et al., "Steviol Glycoside Rebaudioside A Induces Glucagon-like Peptide-1 and Peptide YY Release in a Porcine ex Vivo Intestinal Model", Journal of Agricultural and Food Chemistry, 2014, 62, pp. 8365-8370; Cited in CN Office Action dated Aug. 28, 2020.

Non-Final Office Action dated Aug. 16, 2021, issued in U.S. Appl. No. 16/516,622. (29 pages).

Extended Search Report dated Jan. 7, 2019, issued in counterpart European Application No. 16818003.2 (5 pages).

* cited by examiner

COMPOSITION CONTAINING CYCLIC DIPEPTIDE AND SWEETENING AGENT

TECHNICAL FIELD

The present invention relates to a composition containing a cyclic dipeptide and a sweetening agent. More specifically, the present invention relates to a composition containing a cyclic dipeptide or a salt thereof and a sweetening agent, wherein the content ratio of the cyclic dipeptide or a salt thereof and the sweetening agent falls within a specified range; use of the composition for accelerating secretion of GLP-1; and a method for accelerating secretion of GLP-1. The present invention also relates to a composition for accelerating GLP-1 secretion containing a specified steviol glycoside as an active ingredient and use of the specified steviol glycoside for accelerating GLP-1 secretion.

BACKGROUND ART

In a modern society, the number of diabetic patients or potential diabetic patients are increasing due to e.g., lifestyle change. Diabetes is a disease caused by abnormal glucose metabolism and has a risk of causing various complications (e.g., diabetic retinopathy, diabetic nephropathy and diabetic neuropathy) by a pathological elevation of blood glucose level (glucose concentration in the blood). Particularly, patients with insulin-independent diabetes (type II diabetes) occupies 90% or more of the (whole) diabetic patients. Because of this, treatment, amelioration or prevention of the insulin-independent diabetes has been strongly desired.

In treatment, amelioration or prevention for diabetes, it is important to properly control the blood glucose level, and various drugs for lowering the blood glucose level have been developed as a diabetes drug. For example, a sulfonyl urea agent which acts on pancreatic β cells to stimulate insulin secretion, has been widely used; however, side effects such as hypoglycemia and gastrointestinal problems are reported. It is also reported that an α-glycosidase inhibitor, which delays digestion/absorption of carbohydrates through the digestive tract, has side effects such as hypoglycemia, abdominal symptom including abdominal distension and increased flatus, and liver dysfunction. Further, as to a biguanide agent, which suppresses glucose release from the liver, gastrointestinal tract disturbance and biotoxicity such as lactic acidosis are concerns. Thus, the safety of the biguanide agent is not necessarily satisfied.

A glucagon-like peptide (GLP-1), which is known as a so-called diet hormone (weight-loss hormone), is incretin consisting of 30 or 31 amino acids and is secreted from enteroendocrine cells, i.e., L cells, in response to dietary ingestion of a fat, a carbohydrate and a protein. Since GLP-1 secretion was found to decline in type II diabetic patients, accelerating secretion of GLP-1 is effective for treating type II diabetes and other related diseases (NPL 1). GLP-1 is also known to increase secretion of insulin in response to normal ingestion of glucose, thereby suppressing appetite (NPL 2).

Under the circumstance, it is reported that a sweetening agent such as glucose, sucrose, sucralose, rebaudioside A has a GLP-1 secretion-accelerating action (NPL 3, 4). It is also reported that stevioside is effective for diabetes treatment (NPL 5). It is further reported that diet soda containing acesulfame potassium and sucralose has a GLP-1 secretion-accelerating action (NPL 6). Particularly, an artificial sweetening agent such as sucralose has little effect on elevation of blood glucose level, an artificial sweetening agent having a GLP-1 secretion-accelerating action is suitable for controlling the blood sugar level of diabetic patients.

CITATION LIST

Non Patent Literature

NPL 1: Journal of Clinical Investigation, 91(3), 301-307 (1993)
NPL 2: Lancet, 359, 824-830 (2002)
NPL 3: Proceedings of the National Academy of Sciences of the United States of America, 104(38), 15069-15074 (2007)
NPL 4: Journal of Agricultural Food Chemistry, 62(33), 8365-8370 (2014)
NPL 5: Metabolism, 53(1), 73-76 (2004)
NPL 6: Journal of Nutritional Science and Vitaminology, 66(2), 69-75 (2013)

SUMMARY OF INVENTION

Technical Problem

An object of the present invention is to provide a composition that can enhance the GLP-1 secretion-accelerating activity of a sweetening agent. Providing a GLP-1 secretion-accelerating composition, use of a material for accelerating GLP-1 secretion and a method for accelerating secretion of GLP-1 is another object of the present invention.

Solution to Problem

The present inventors conducted diligent studies on the aforementioned objects. As a result, they focused on taking advantage of a cyclic dipeptide or a salt thereof. The cyclic dipeptide is a dipeptide having a cyclic structure, which is produced by dehydration condensation of the amino group and the carboxyl group respectively present at the terminals of a linear dipeptide, and whose various physiological activities have recently attracted attention. The present inventors found that if the content ratio of a cyclic dipeptide or a salt thereof and a sweetening agent in a composition is controlled to fall within a specified range, GLP-1 secretion-accelerating activity derived from a single sweetening agent can be enhanced.

The present inventors further found that a specified steviol glycoside has a remarkable GLP-1 secretion-accelerating effect and arrived at accomplishment of the present invention.

More specifically, the present invention relates to, but is not limited to, the following aspects.

(1) A composition containing a cyclic dipeptide or a salt thereof and a sweetening agent, wherein
the content of the cyclic dipeptide or a salt thereof in the composition is $5.0 \times 10^{-4}$ ppm to $1.5 \times 10^{4}$ ppm; and
the content ratio of the cyclic dipeptide or a salt thereof and the sweetening agent is 1:30 to 1:15000000.

(2) The composition according to (1), wherein the cyclic dipeptide includes either one or both of cyclo(glycyl-tyrosine) [Cyclo(Gly-Tyr)] and cyclo(leucyl-phenylalanine) [Cyclo(Leu-Phe)].

(3) The composition according to (1) or (2), wherein the sweetening agent includes one or two or more members selected from the group consisting of glucose, sucralose, acesulfame potassium, aspartame and steviol glycoside.

(4) The composition according to any one of (1) to (3), wherein
the sweetening agent includes glucose, and
the content ratio of the cyclic dipeptide or a salt thereof and glucose is 1:3000 to 1:15000000.

(5) The composition according to any one of (1) to (3), wherein
the sweetening agent includes sucralose, and
the content ratio of the cyclic dipeptide or a salt thereof and sucralose is 1:60 to 1:300000.

(6) The composition according to any one of (1) to (3), wherein
the sweetening agent includes acesulfame potassium,
the content ratio of the cyclic dipeptide or a salt thereof and acesulfame potassium is 1:30 to 1:150000.

(7) The composition according to any one of (1) to (3), wherein
the sweetening agent includes aspartame, and
the content ratio of the cyclic dipeptide or a salt thereof and aspartame is 1:30 to 1:150000.

(8) The composition according to any one of (1) to (3), wherein
the sweetening agent includes steviol glycoside, and
the steviol glycoside is one or two or more members selected from the group consisting of stevioside, rebaudioside A, rebaudioside B, rebaudioside C and rebaudioside D.

(9) The composition according to (8), wherein
the steviol glycoside includes stevioside, and
the content ratio of the cyclic dipeptide or a salt thereof and stevioside is 1:30 to 1:1:20000.

(10) The composition according to (8), wherein
the sweetening agent includes rebaudioside A, and
the content ratio of the cyclic dipeptide or a salt thereof and rebaudioside A is 1:30 to 1:1:20000.

(11) The composition according to (8), wherein
the sweetening agent includes rebaudioside D, and
the content ratio of the cyclic dipeptide or a salt thereof and rebaudioside D is 1:30 to 1:1:20000.

(12) The composition according to any one of (1) to (11), wherein the content of the sweetening agent is 1.0 ppm to $6.0 \times 10^5$ ppm.

(13) The composition according to any one of (1) to (12), wherein the content of the sweetening agent is 0.5 wt % to 600 wt %° in terms of sucrose concentration.

(14) The composition according to any one of (1) to (13), wherein the cyclic dipeptide or a salt thereof is obtained from a soybean peptide, a tea peptide or a malt peptide.

(15) The composition according to any one of (1) to (14), having a GLP-1 secretion-accelerating action.

(16) The composition according to any one of (1) to (15), for ameliorating glucose metabolism, suppressing appetite or preventing or ameliorating diabetes or obesity.

(17) Use of a composition containing a cyclic dipeptide or a salt thereof and a sweetening agent, for accelerating secretion of GLP-1, wherein
the content of the cyclic dipeptide or a salt thereof in the composition is $5.0 \times 10^{-4}$ ppm to $1.5 \times 10^4$ ppm, and
the content ratio of the cyclic dipeptide or a salt thereof and the sweetening agent is 1:30 to 1:15000000.

(18) The use according to (17), wherein the cyclic dipeptide includes either one or both of the cyclo(glycyl-tyrosine) [Cyclo(Gly-Tyr)] and cyclo(leucyl-phenylalanine) [Cyclo(Leu-Phe)].

(19) The use according to (17) or (18), wherein the sweetening agent includes one or two or more members selected from the group consisting of glucose, sucralose, acesulfame potassium, aspartame and steviol glycoside.

(20) A method for accelerating secretion of GLP-1 by using a composition containing a cyclic dipeptide or a salt thereof and a sweetening agent, wherein
the content of the cyclic dipeptide or a salt thereof in the composition is $5.0 \times 10^{-4}$ ppm to $1.5 \times 10^4$ ppm, and
the content ratio of the cyclic dipeptide or a salt thereof and the sweetening agent is 1:30 to 1:15000000.

(21) The method according to (20), wherein the cyclic dipeptide includes either one or both of cyclo(glycyl-tyrosine) [Cyclo(Gly-Tyr)] and cyclo(leucyl-phenylalanine) [Cyclo(Leu-Phe)].

(22) The method according to (20) or (21), wherein the sweetening agent includes one or two or more members selected from the group consisting of glucose, sucralose, acesulfame potassium, aspartame and steviol glycoside.

(23) A GLP-1 secretion-accelerating composition containing steviol glycoside as an active ingredient, wherein
the steviol glycoside includes at least one of rebaudioside B and rebaudioside D.

(24) The GLP-1 secretion-accelerating composition according to claim 23, for ameliorating glucose metabolism, suppressing appetite or preventing or ameliorating diabetes or obesity.

(25) The GLP-1 secretion-accelerating composition according to claim 23, provided with a label indicating a function developed by a GLP-1 secretion-accelerating action.

(26) The GLP-1 secretion-accelerating composition according to claim 25, wherein the indication of a function is selected from the group consisting of "ameliorating glucose metabolism", "preventing diabetes", "ameliorating diabetes", "suppressing an elevation of postprandial blood glucose level", "controlling blood glucose level", "suppressing appetite", "preventing obesity" and "ameliorating obesity".

(27) Use of steviol glycoside for accelerating GLP-1 secretion, wherein
the steviol glycoside includes at least one of rebaudioside B and rebaudioside D.

(28) A method for accelerating GLP-1 secretion by using steviol glycoside as an active ingredient, wherein
the steviol glycoside includes at least one of rebaudioside B and rebaudioside D.

Advantageous Effects of Invention

Owing to the present invention, it is possible to provide a composition enhanced in GLP-1 secretion-accelerating activity derived from a single sweetening agent. Owing to the present invention, it is also possible to provide a GLP-1 secretion-accelerating composition containing a specified steviol glycoside as an active ingredient. Since glucose metabolism amelioration action can be obtained by accelerating GLP-1 secretion, e.g., an effect of suppressing elevation of postprandial blood glucose level and effect of preventing or ameliorating diabetes or obesity are exerted by ingestion of the composition according to the present invention.

The cyclic dipeptide contained in the composition according to the present invention is contained in e.g., a heat-treated material of a plant-derived peptide and thus high in safety. Because of this, a risk of developing a serious side effect for the composition according to the present invention is considered to be extremely low.

Figure 2:
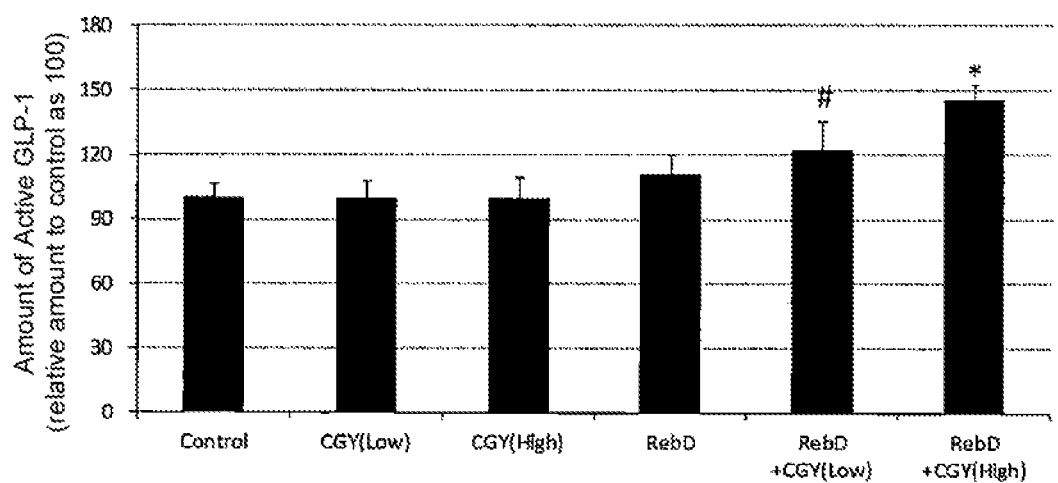

FIG. 2 is a graph showing the effect of rebaudioside D and rebaudioside D+Cyclo(Gly-Tyr) on GLP-1 secretion amount when NCI-H716 cells are cultured for one hour in the presence of each of them.

Figure 3:
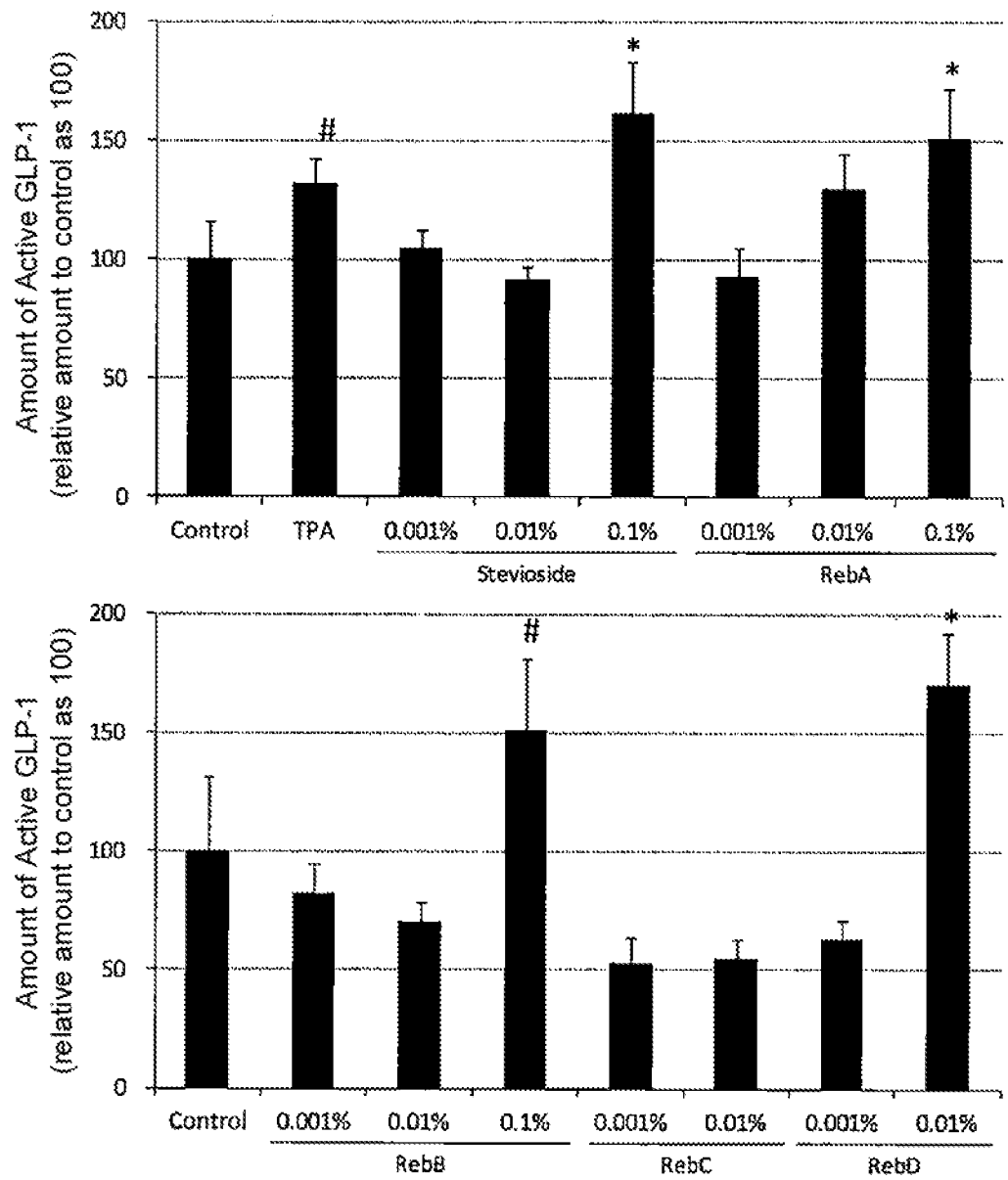

FIG. 3 is a graph showing the effects of stevioside, rebaudioside A, rebaudioside B, rebaudioside C and rebaudioside D on GLP-1 secretion amount when NCI-H716 cells are cultured for one hour in the presence of each of them.

DESCRIPTION OF EMBODIMENTS

1. Cyclic Dipeptide or a Salt Thereof

In the specification, "cyclic dipeptide" refers to a cyclic dipeptide constituted of amino acids as a structural unit and having a diketopiperazine structure produced by dehydration condensation of an amino group and a carboxyl group of amino acids. Note that, in the specification, a cyclic dipeptide or a salt thereof is sometimes collectively referred to simply as a cyclic dipeptide. In the specification, as long as amino acids constituting a cyclic dipeptide are the same, the order (either one of them is described first) of the amino acids in description is not limited; for example, [Cyclo(Gly-Tyr)] and [Cyclo(Tyr-Gly)] represent the same cyclic dipeptide.

In a cyclic dipeptide, since two amino acids are bound at the terminal portions via an amide bond (more specifically, a cyclic dipeptide has a cyclic structure formed by binding an amino terminal and a carboxy terminal via an amide bond), the cyclic dipeptide has a high solubility to lipid, compared to a linear dipeptide (particularly, a linear dipeptide having the same amino acid constitution) having polar groups, i.e., a terminal carboxyl group and amino group, exposed. Because of this, the cyclic dipeptide is excellent in permeability through the digestive tract and the membrane, compared to the linear dipeptide. This is apparent from the results of permeability tests of a compound using a rat everted sac and reported in the past (J. Pharmacol, 1998, 50: 167-172). In addition, in consideration of the specific structure of a cyclic dipeptide, the cyclic dipeptide is presumably high in resistance to various peptidases.

The cyclic dipeptide or a salt thereof to be contained in the present invention is not particularly limited; however, it is preferable that, for example, either one or both of cyclo (glycyl-tyrosine) [Cyclo(Gly-Tyr)] and cyclo(leucyl-phenylalanine) [Cyclo(Leu-Phe)] are contained.

In the specification, "a salt of a cyclic dipeptide" refers to any one of the pharmacologic acceptable salts (including inorganic salts and organic salts) of a cyclic dipeptide. Examples thereof include, but are not particularly limited to, a sodium salt, a potassium salt, a calcium salt, a magnesium salt, an ammonium salt, a hydrochloride, a sulfate, a nitrate, a phosphate and an organic acid salt (e.g., acetate, citrate, maleate, malate, oxalate, lactate, succinate, fumarate, propionate, formate, benzoate, picrate, benzenesulfonate, trifluoroacetate) of a cyclic dipeptide as mentioned above. A salt of a cyclic dipeptide can be easily prepared by those skilled in the art in accordance with a method known in the art.

The cyclic dipeptide to be used in the present invention can be prepared in accordance with a method known in the art; for example, a chemical synthesis method, an enzymatic method or a microbial fermentation method; may be synthesized by dehydration and cyclization of a linear peptide; and can be prepared in accordance with the method described in e.g., Japanese Patent Laid-Open No. 2003-252896, Journal of Peptide Science, 10, 737-737, 2004 and International Publication No. WO2014/200000. For example, a plant-derived peptide, which is obtained by subjecting a raw material containing a plant-derived protein to an enzyme treatment or a heat treatment, can be further subjected to a heat treatment at a high temperature to successfully obtain a heat treated plant-derived peptide material rich in cyclic dipeptide. Note that, the obtained heat treated plant-derived peptide material, if desired, may be subjected to a treatment such as filtration, centrifugation, concentration, ultrafiltration, lyophilization and powderization. If the amount of a specified cyclic dipeptide in the heat treated plant-derived peptide material fails to satisfy a desired content, another plant-derived peptide, a commercially available product or a synthetic product thereof may be appropriately added to make up for the shortage of the specified cyclic dipeptide.

In the present invention, a cyclic dipeptide or a salt thereof may be obtained from a plant-derived peptide such as a soybean peptide, a tea peptide or a malt peptide; and from a heat-treated material of a plant-derived peptide such as a heat-treated soybean peptide product, a heat-treated tea peptide product or a heat-treated malt peptide product.

2. Plant-Derived Peptide

In the specification, the "plant-derived peptide" is not particularly limited and, for example, a soybean peptide, a tea peptide or a malt peptide can be used. The plant-derived peptide may be prepared from a plant-derived protein or a raw material containing a protein, and a commercially available plant-derived peptide may be used.

2-1. Soybean Peptide

In the specification, the "soybean peptide" refers to a low molecular-weight peptide, which is obtained by applying an enzyme treatment and/or a heat treatment to a soy protein to reduce the molecular weight thereof. As the soy beans (scientific name: Glycine max) to be used as a raw material any soy beans can be used without limitation in e.g., species and production area, and a product during a processing stage, such as pulverized soy beans, can be used.

2-2. Tea Peptide

In the specification, the "tea peptide" refers to a tea-derived low molecular-weight peptide, which is obtained by applying an enzyme treatment and/or a heat treatment to a tea (including tea leaves and used tea leaves) extract to reduce the molecular weight of a protein. As raw material tea leaves to be extracted, sites of a tea tree (scientific name: *Camellia sinensis*) such as tea leaves and stems, which are the sites drinkable by brewing, can be used. The morphological feature (large leaves or powder) of the site is not limited. The harvest period of tea leaves can be appropriately selected in accordance with desired taste and flavor.

2-3. Malt Peptide

In the specification, the "malt peptide" refers to a malt-derived low molecular-weight peptide, which is obtained by applying to an enzyme treatment and/or heat treatment to an extract obtained from malt or a pulverized material thereof to reduce the molecular weight of a protein. As the malt peptide to be used as a raw material, any malt peptide can be used without limitation in e.g., species and production area; however, particularly malted barley, which is a germinated barley seed, is suitably used. Note that, in the specification, the malted barley sometimes simply referred to as malt.

3. Sweetening Agent

In the composition according to the present invention, a sweetening agent, such as a natural sweetening agent, a sugar alcohol and an artificial sweetening agent, can be used.

Examples of the natural sweetening agent include, but are not limited to, glucose, fructose, steviol glycoside, mogrol glycoside, glycyrrhizinic acid glycoside, maltose, sucrose, lactose, rare sugar, high fructose syrup, fructose glucose syrup, glucose fructose syrup, oligosaccharide, honey, sugarcane juice (molasses), sugar (e.g., white sugar, soft brown sugar, brown sugar, refined sugar), maple syrup, molasses and starch syrup. Examples of the sugar alcohol include, but are not limited to, erythritol, xylitol, sorbitol, maltitol and mannitol. Examples of the artificial sweetening agent include, but are not limited to, sucralose, acesulfame potassium, aspartame, saccharin, alitame and neotame.

In the sweetening agent to be used in the present invention, one or two or more members selected from the group consisting of a steviol glycoside such as glucose, sucralose, acesulfame potassium, aspartame, fructose, saccharin, erythritol, xylitol, sorbitol, maltitol, mannitol, stevioside and rebaudioside A, mogrol glycoside and glycyrrhizinic acid glycoside, and more preferably, one or two or more members selected from the group consisting of glucose, sucralose, acesulfame potassium and aspartame, are contained.

3-1. Steviol Glycoside

Leaves of *Stevia rebaudiana* contain a secondary metabolite, i.e., a kind of diterpenoid, called as steviol. A glycoside of steviol, i.e., steviol glycoside, is sweet, the sweetness of which is about 300 times as strong as that of sugar. Because of this, steviol glycoside is used as a calorie-less sweetening agent in the food industry. Steviol is modified with a sugar finally up to a glycoside called as rebaudioside (Reb). A precursor thereof steviol trisaccharide glucoside, i.e., stevioside, is most abundantly present. As rebaudioside, a plurality of molecular species such as RebA, RebB, RebC and RebD, are known as described, for example, in WO2013/146555. The chemical structures of stevioside, RebA. RebB, RebC and RebD, are shown below.

[Formula 1]

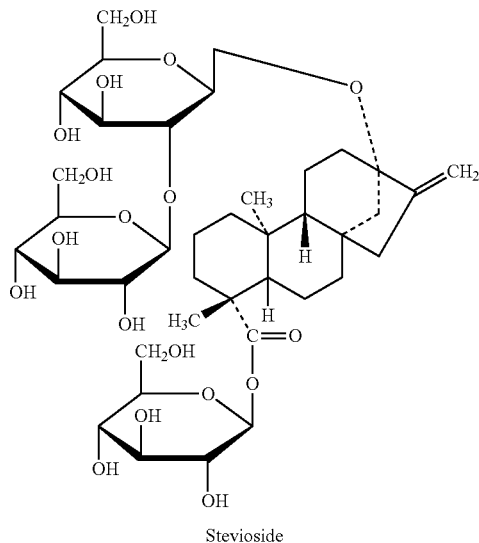

Stevioside

[Formula 2]

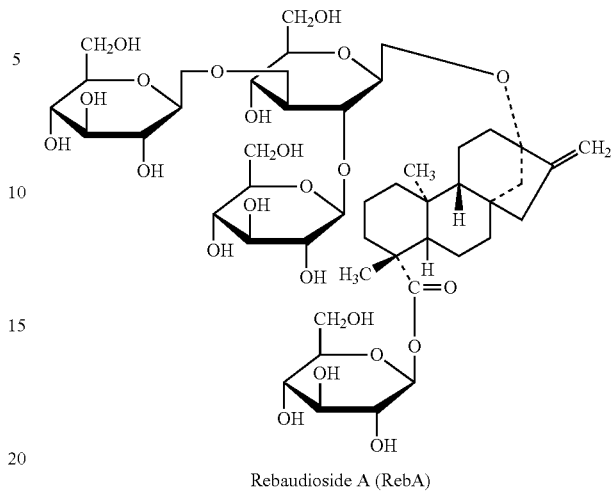

Rebaudioside A (RebA)

[Formula 3]

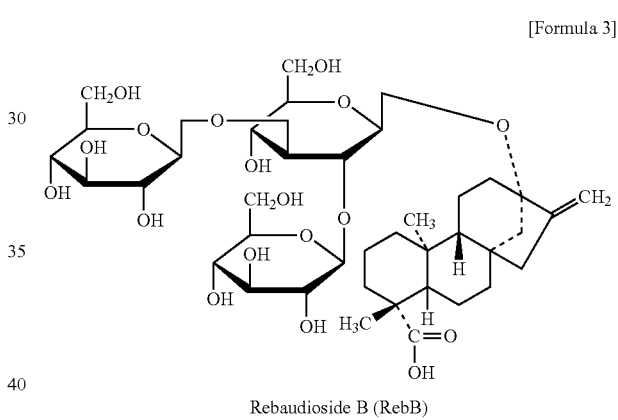

Rebaudioside B (RebB)

[Formula 4]

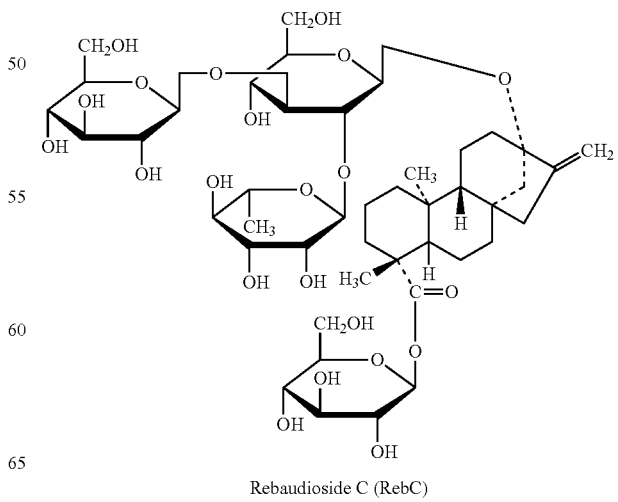

Rebaudioside C (RebC)

-continued

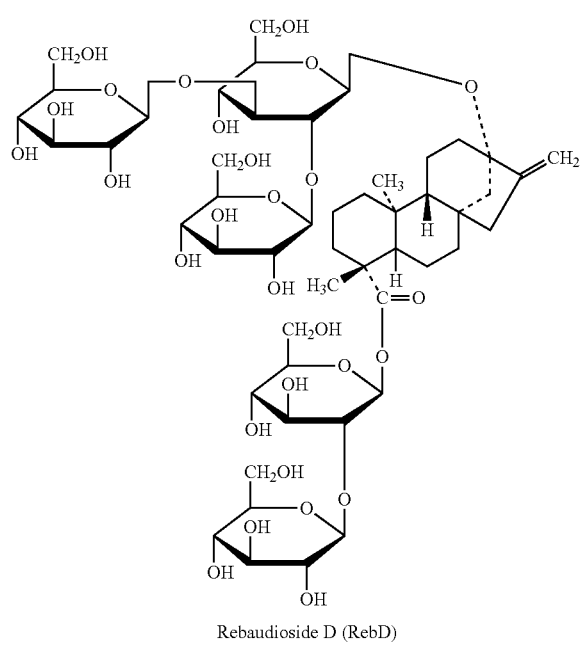

Rebaudioside D (RebD)

[Formula 5]

In the present invention, in the case where steviol glycoside is used as the sweetening agent, the sweetening agent includes one or two or more members selected from the group consisting of stevioside, RebA, RebB, RebC and RebD, and more preferably, one or two or more members selected from the group consisting of stevioside, RebA and RebD. Examples are not limited to these.

4. Composition

An embodiment of the present invention is a composition containing a cyclic dipeptide or a salt thereof and a sweetening agent, in which the content ratio of the cyclic dipeptide or a salt thereof and the sweetening agent falls within a specified range.

4-1. Content Ratio of Cyclic Dipeptide and Sweetening Agent

In the present invention, it is important that the content ratio of a cyclic dipeptide or a salt thereof and the sweetening agent falls within a specified range. Although the content ratio of a cyclic dipeptide or a salt thereof and the sweetening agent in a composition (the total amount of cyclic dipeptides or salts thereof in a composition: the content of a sweetening agent in the composition) is not particularly limited; however, the content ratio is more specifically, 1:30 or more, 1:60 or more, 1:75 or more, 1:150 or more, 1:300 or more, 1:3000 or more, 1:7500 or more or 1:15000 or more; and 1:15000000 or less, 1:6000000 or less, 1:3000000 or less, 300000 or less, 1:150000 or less, 1:120000 or less or 1:60000 or less. Typically, the content ratio of a cyclic dipeptide or a salt thereof and the sweetening agent in a composition falls in the range of 1:30 to 1:15000000, preferably 1:3000 to 1:15000000, 1:7500 to 1:6000000, 1:15000 to 1:3000000, 1:60 to 1:300000, 1:150 to 1:120000, 1:300 to 1:60000, 1:30 to 1:150000, 1:75 to 1:60000 or 1:150 to 1:30000.

The cyclic dipeptide or a salt thereof to be contained in the present invention is not particularly limited and either one or both of cyclo(glycyl-tyrosine) [Cyclo(Gly-Tyr)] and cyclo(leucyl-phenylalanine) [Cyclo(Len-Phe)] are preferably contained.

The sweetening agent to be contained in the present invention is not particularly limited, and preferably one or two or more members selected from the group consisting of glucose, sucralose, acesulfame potassium, aspartame, fructose, saccharin, erythritol xylitol, sorbitol, maltitol, mannitol, stevioside, rebaudioside A, rebaudioside B, rebaudioside C and rebaudioside D; and more preferably, one or two or more members selected from the group consisting of glucose, sucralose, acesulfame potassium, aspartame, stevioside, rebaudioside A, rebaudioside B, rebaudioside C and rebaudioside D.

In the case where the sweetening agent includes glucose, the content ratio of a cyclic dipeptide or a salt thereof and glucose in the composition according to the present invention is preferably 1:3000 to 1:15000000, more preferably 1:7500 to 1:6000000 and still more preferably 1:15000 to 1:3000000.

In the case where the sweetening agent includes sucralose, the content ratio of a cyclic dipeptide or a salt thereof and sucralose in the composition according to the present invention is preferably 1:60 to 1:300000, more preferably 1:150 to 1:120000 and still more preferably 1:300 to 1:60000.

In the case where the sweetening agent includes acesulfame potassium, the content ratio of a cyclic dipeptide or a salt thereof and acesulfame potassium in the composition according to the present invention is preferably 1:30 to 1:150000, more preferably 1:75 to 1:60000 and still more preferably 1:150 to 1:30000.

In the case where the sweetening agent includes aspartame, the content ratio of a cyclic dipeptide or a salt thereof and aspartame in the composition according to the present invention is preferably 1:30 to 1:150000, more preferably 1:75 to 1:60000 and still more preferably 1:150 to 1:30000.

In the case where the sweetening agent includes steviol glycoside, the content ratio of a cyclic dipeptide or a salt thereof and steviol glycoside in the composition according to the present invention is preferably 1:30 to 1:250000, more preferably 1:40 to 1:150000 and still more preferably 1:50 to 1:100000.

In the case where the sweetening agent includes stevioside, the content ratio of a cyclic dipeptide or a salt thereof and stevioside in the composition according to the present invention is preferably 1:30 to 1:50000, more preferably 1:40 to 1:30000 and still more preferably 1:50 to 1:20000.

In the case where the sweetening agent includes rebaudioside A, the content ratio of a cyclic dipeptide or a salt thereof and rebaudioside A in the composition according to the present invention is preferably 1:30 to 1:50000, more preferably 1:40 to 1:30000 and still more preferably 1:50 to 1:20000.

In the case where the sweetening agent includes rebaudioside B, the content ratio of a cyclic dipeptide or a salt thereof and rebaudioside B in the composition according to the present invention is preferably 1:30 to 1:50000, more preferably 1:40 to 1:30000 and still more preferably 1:50 to 1:20000.

In the case where the sweetening agent includes rebaudioside C, the content ratio of a cyclic dipeptide or a salt thereof and rebaudioside C in the composition according to the present invention is preferably 1:30 to 1:50000, more preferably 1:40 to 1:30000 and still more preferably 1:50 to 1:20000.

In the case where the sweetening agent includes rebaudioside D, the content ratio of a cyclic dipeptide or a salt thereof and rebaudioside D in the composition according to the present invention is preferably 1:30 to 1:50000, more preferably 1:40 to 1:30000 and still more preferably 1:50 to 1:20000.

4-2. Content of Cyclic Dipeptide

The content of a cyclic dipeptide or a salt thereof in the composition according to the present invention, is not particularly limited as long as the content ratio of an amino acid or a salt thereof and a cyclic dipeptide or a salt thereof in the composition falls in a range as mentioned above, in view of e.g., the dosage form and the administration method thereof. For example, in the case where a plant-derived peptide such as a soybean peptide, a tea peptide or a malt peptide is used as a raw material, the content of a cyclic dipeptide or a salt thereof in the composition according to the present invention is, for example, $5.0 \times 10^{-4}$ ppm or more, preferably $1.0 \times 10^{-3}$ ppm or more, more preferably $5.0 \times 10^{-3}$ ppm or more and still more preferably $1.0 \times 10^{-2}$ ppm or more, $1.5 \times 10^4$ ppm or less, preferably $1.0 \times 10^4$ ppm or less, more preferably $5.0 \times 10^3$ ppm or less, and more preferably $2.5 \times 10^3$ ppm or less; and typically, $5.0 \times 10^{-4}$ ppm to $1.5 \times 10^4$ ppm, preferably $1.0 \times 10^{-3}$ ppm to $1.0 \times 10^4$ ppm, more preferably $5.0 \times 10^{-3}$ ppm to $5.0 \times 10^3$ ppm and still more preferably $1.0 \times 10^{-2}$ ppm to $2.5 \times 10^3$ ppm. In the case where a plant-derived peptide such as a soybean peptide, a tea peptide or a malt peptide is used as a raw material, the individual contents of cyclic dipeptides (e.g., cyclo(glycyl-tyrosine) [Cyclo(Gly-Tyr)] and cyclo(leucyl-phenylalanine) [Cyclo(Leu-Phe)]) and the salts corresponding to these cyclic dipeptides in the composition according to the present invention are not particularly limited and are, for example, $5.0 \times 10^{-6}$ ppm or more, preferably $5.0 \times 10^{-5}$ ppm or more, more preferably $5.0 \times 10^{-4}$ ppm or more and still more preferably $5.0 \times 10^{-3}$ ppm or more; $1.5 \times 10^2$ ppm or less, preferably $1.0 \times 10^2$ ppm or less, more preferably 50 ppm or less, more preferably 25 ppm or less; and typically $5.0 \times 10^{-6}$ ppm to $1.5 \times 10^2$ ppm, preferably $5.0 \times 10^{-5}$ ppm to $1.0 \times 10^2$ ppm, more preferably $5.0 \times 10^{-4}$ ppm to 50 ppm and still more preferably $5.0 \times 10^{-3}$ ppm to 25 ppm. Note that, unless otherwise specified. "ppm" used in the specification means ppm in weight/volume (w/v). 1.0 ppm is converted as $1.0 \times 10^{-3}$ mg/mL and $1.0 \times 10^{-4}$ wt %.

The content of a cyclic dipeptide or a salt thereof blended in the composition according to the present invention can be measured by a known method, for example, LC-MS/MS.

In the case of using a synthesized product or a purified product as a cyclic dipeptide or a salt thereof the content of the cyclic dipeptide or a salt thereof in the composition according to the present invention is not particularly limited and is, for example, $5.0 \times 10^{-4}$ ppm or more, preferably $1.0 \times 10^{-3}$ ppm or more, more preferably $5.0 \times 10^{-3}$ ppm or more and still more preferably $1.0 \times 10^{-2}$ ppm or more; $1.5 \times 10^4$ ppm or less, preferably $1.0 \times 10^4$ ppm or less, more preferably $5.0 \times 10^3$ ppm or less, more preferably $2.5 \times 10^3$ ppm or less; and typically $5.0 \times 10^{-4}$ ppm to $1.5 \times 10^4$ ppm, preferably $1.0 \times 10^{-3}$ ppm to $1.0 \times 10^4$ ppm, more preferably $5.0 \times 10^{-3}$ ppm to $5.0 \times 10^3$ ppm and still more preferably $1.0 \times 10^{-2}$ ppm to $2.5 \times 10^3$ ppm. In the case of using a synthesized product or a purified product as a cyclic dipeptide or a salt thereof, the individual contents of cyclic dipeptides (e.g., cyclo(glycyl-tyrosine) [Cyclo(Gly-Tyr)] and cyclo(leucyl-phenylalanine) [Cyclo(Leu-Phe)]) and the salts corresponding to these cyclic dipeptides in the composition according to the present invention are not particularly limited and are, for example, $5.0 \times 10^{-6}$ ppm or more, preferably $5.0 \times 10^{-5}$ ppm or more, more preferably $5.0 \times 10^{-4}$ ppm or more and still more preferably $5.0 \times 10^{-3}$ ppm or more; $1.5 \times 10^2$ ppm or less, preferably $1.0 \times 10^2$ ppm or less, more preferably 50 ppm or less, more preferably 25 ppm or less; and typically $5.0 \times 10^{-6}$ ppm to $1.5 \times 10^2$ ppm, preferably $5.0 \times 10^{-5}$ ppm to $1.0 \times 10^2$ ppm, more preferably $5.0 \times 10^{-4}$ ppm to 50 ppm and still more preferably $5.0 \times 10^{-3}$ ppm to 25 ppm.

4-3. Content of Sweetening Agent

The content of a sweetening agent in the composition according to the present invention is not particularly limited as long as the content ratio of a cyclic dipeptide or a salt thereof and a sweetening agent in a composition falls within a range as described above, in view of e.g., dosage form and administration method. For example, the total amount of sweetening agents in the composition according to the present invention is 1.0 ppm or more, 10 ppm or more, 30 ppm or more, $1.0 \times 10^2$ ppm or more, $1.0 \times 10^3$ ppm or more and $1.0 \times 10^4$ ppm or more; $6.0 \times 10^5$ ppm or less, $4.0 \times 10^5$ ppm or less, $2.0 \times 10^5$ ppm or less, $1.0 \times 10^5$ ppm or less, $5.0 \times 10^4$ ppm or less, $1.0 \times 10^4$ ppm or less; and typically 1.0 ppm to $6.0 \times 10^5$ ppm, $1.0 \times 10^2$ ppm to $6.0 \times 10^5$ ppm, 1.0 ppm to $1.0 \times 10^5$ ppm and 10 ppm to $1.0 \times 10^5$ ppm. In the case where the sweetening agent includes glucose, the content of glucose in the composition according to the present invention is preferably $1.0 \times 10^2$ ppm to $6.0 \times 10^5$ ppm, more preferably $1.0 \times 10^3$ ppm to $4.0 \times 10^5$ ppm and still more preferably $1.0 \times 10^4$ ppm to $2.0 \times 10^5$ ppm. In the case where the sweetening agent includes sucralose, the content of sucralose in the composition according to the present invention is preferably 1.0 ppm to $1.0 \times 10^5$ ppm, more preferably 10 ppm to $5.0 \times 10^4$ ppm and still more preferably 30 ppm to $1.0 \times 10^4$ ppm. In the case where the sweetening agent includes acesulfame potassium, the content of acesulfame potassium in the composition according to the present invention is preferably 10 ppm to $1.0 \times 10^5$ ppm, more preferably $1.0 \times 10^2$ ppm to $5.0 \times 10^4$ ppm and still more preferably $1.0 \times 10^3$ ppm to $1.0 \times 10^4$ ppm. In the case where the sweetening agent includes aspartame, the content of aspartame in the composition according to the present invention is preferably 10 ppm to $1.0 \times 10^5$ ppm, more preferably $1.0 \times 10^2$ ppm to $5.0 \times 10^4$ ppm and still more preferably $1.0 \times 10^3$ ppm to $1.0 \times 10^4$ ppm. In the case where the sweetening agent includes steviol glycoside, the content of steviol glycoside in the composition according to the present invention is preferably 1.0 ppm to $5.0 \times 10^5$ ppm, more preferably 10 ppm to $2.5 \times 10^5$ ppm and still more preferably 30 ppm to $5.0 \times 10^4$ ppm. In the case where the sweetening agent includes stevioside, the content of stevioside in the composition according to the present invention is preferably 1.0 ppm to $1.0 \times 10^5$ ppm, more preferably 10 ppm to $5.0 \times 10^4$ ppm and still more preferably 30 ppm to $1.0 \times 10^4$ ppm. In the case where the sweetening agent includes rebaudioside A, the content of rebaudioside A in the composition according to the present invention is preferably 1.0 ppm to $1.0 \times 10^5$ ppm, more preferably 10 ppm to $5.0 \times 10^4$ ppm and still more preferably 30 ppm to $1.0 \times 10^4$ ppm. In the case where the sweetening agent includes rebaudioside B, the content of rebaudioside B in the composition according to the present invention is preferably 1.0 ppm to $1.0 \times 10^5$ ppm, more preferably 10 ppm to $5.0 \times 10^4$ ppm and still more preferably 30 ppm to $1.0 \times 10^4$ ppm. In the case where the sweetening agent includes rebaudioside C, the content of rebaudioside C in the composition according to the present invention is preferably, preferably 1.0 ppm to $1.0 \times 10^5$ ppm, more preferably 10 ppm to $5.0 \times 10^4$ ppm and still more preferably 30 ppm to $1.0 \times 10^4$ ppm. In the case where the sweetening agent includes rebaudioside D, the content of rebaudioside D in the composition according to the present invention is preferably, 1.0 ppm to $1.0 \times 10^5$ ppm, more preferably 10 ppm to $5.0 \times 10^4$ ppm and still more preferably 30 ppm to $1.0 \times 10^4$ ppm.

The content of a sweetening agent in the composition according to the present invention can be defined by the sucrose concentration (wt %) calculated and converted based on the sweetness degree of each sweetening agent. In the specification, the "degree of sweetness" is the degree of sweetness based on the sweetness of sucrose and corresponds to sucrose concentration (wt %) of an aqueous sucrose solution. For example, a sweetness degree of 2 corresponds to the sweetness of a 2 wt % aqueous sucrose solution. The sweetness degrees of individual sweetening agents in the case where the sweetness degree of sucrose is specified as 1 will be described below: glucose: 0.60 to 0.70, sucralose: 600, acesulfame potassium: 200, aspartame: 100 to 200, saccharin: 200 to 700, erythritol: 0.75 to 0.80, xylitol: 0.60, sorbitol: 0.60 to 0.70, maltitol: 0.80 to 0.90, mannitol: 0.60, fructose: 1.73, stevioside: 300, rebaudioside A: 450, rebaudioside B: 300, rebaudioside C: 30, rebaudioside D: 285.

Note that, to control the degree of sweetness, the amount of natural sweetening agent, sugar alcohol or artificial sweetening agent to be used may be controlled.

The content of a sweetening agent in the composition according to the present invention is not particularly limited as long as the content ratio of the cyclic dipeptide or a salt thereof and the sweetening agent in a composition falls within a range as described above in view of e.g., the dosage form and the administration method thereof. For example, the content of a sweetening agent in terms of sucrose concentration (wt %) is preferably 1.0 wt % or more, more preferably 1.5 wt % or more and still more preferably 1.8 wt % or more. The upper limit of the sweetness degree of the composition according to the present invention is preferably 600 wt % or less, more preferably 400 wt % or less and still more preferably 360 wt % or less. Typically, the content of a sweetening agent in the composition according to the present invention in terms of sucrose concentration (wt %) is preferably 1.0 wt % to 600 wt %, more preferably 1.5 wt % to 400 wt % and still more preferably 1.8 wt % to 360 wt %.

The concentration of a sweetening agent blended in the composition according to the present invention can be measured by a known method such as HPLC.

The composition according to the present invention may be prepared in accordance with a known method for producing a composition, for example, by mixing a predetermined amount of a cyclic dipeptide or a salt thereof or a sweetening agent as mentioned above to a raw material for use in preparing a known composition, or may be prepared by adding a cyclic dipeptide or a salt thereof or a sweetening agent as mentioned above to a ready-made known composition so as to satisfy the predetermined amount, dissolving and/or suspending them. Note that, the known composition may originally contain a cyclic dipeptide or a salt thereof or a sweetening agent as mentioned above. The composition according to the present invention can be prepared by appropriately blending a cyclic dipeptide or a salt thereof and a sweetening agent as mentioned above as long as the content ratio of the cyclic dipeptide or a salt thereof and the sweetening agent falls within the predetermined range.

4-4. Mechanism of Action

A glucagon-like peptide (GLP-1) known as a so-called diet hormone (weight-loss hormone) is incretin consisting of 30 or 31 amino acids and secreted from L cells, i.e., enteroendocrine cells, in response to ingestion of a fat, a carbohydrate and a protein derived from diet. Since the secretion level of GLP-1 is low in type II diabetic patients, accelerating secretion of GLP-1 is effective for treating type II diabetes and other related diseases.

A sweetening agent, particularly an artificial sweetening agent such as sucralose, accelerates GLP-1 secretion and accelerates insulin secretion without increasing a blood glucose level. Due to the function, the sweetening agent is known to be useful for controlling a blood sugar level in type II diabetic patients. Accordingly, more powerful and excellent carbohydrate metabolism ameliorating action can be obtained by enhancing GLP-1 secretion-accelerating activity derived from a sweetening agent, with the result that an effect of suppressing elevation of a postprandial blood glucose level and preventing or ameliorating effect for diabetes or obesity can be obtained. Further, GLP-1 increases insulin secretion in response to normal glucose ingestion and suppresses appetite. Accordingly, more powerful appetite suppression effect can be obtained by enhancing GLP-1 secretion-accelerating activity derived from a sweetening agent.

4-5. Other Components

In the composition according to the present invention, for example, a raw material containing a cyclic dipeptide or a salt thereof as mentioned above and a sweetening agent specified above may contain any additives or components used in ordinary agents. Examples of these additives and/or components include, but are not limited to, physiologically active ingredients such as vitamins, minerals, nutrient components and fragrances; diluents, binders, emulsifiers, tonicity agents (isotonic agents), buffers, solubilizers, antiseptic agents, stabilizers, antioxidants, colorants, coagulants, and coating agents to be blended in formulating a preparation.

4-6. Use

The composition according to the present invention can strongly enhance a GLP-1 secretion-accelerating effect derived from a single sweetening agent, by controlling the content ratio of a cyclic dipeptide or a salt thereof and a sweetening agent to fall within a specified range. Owing to this, a glucose metabolism ameliorating effect can be obtained. Thus, the composition according to the present invention can be used for treating, preventing or ameliorating diabetes or obesity, or treating, preventing or ameliorating diabetes related diseases. By enhancing GLP-1 secretion-accelerating effect derived from a single sweetening agent, a more powerful appetite suppression effect can be obtained. Accordingly, an embodiment of the present invention is a composition for ameliorating glucose metabolism, suppressing appetite, treating, preventing or ameliorating diabetes or obesity or treating, preventing or ameliorating diabetes related diseases.

Note that, in the specification, diabetes related diseases are not particularly limited and, for example, diabetic hypertension, diabetic retinopathy, diabetic nephropathy and diabetic neurosis are mentioned. Accordingly, the composition according to the present invention can be used for treating, preventing or ameliorating e.g., diabetic hypertension, diabetic retinopathy, diabetic nephropathy and diabetic neurosis.

Examples of the composition according to the present invention include, but are not limited to, drugs, drinks, foods, and cosmetics. Specific examples of the drinks of the present invention may include oolong tea drinks, tea drinks, green tea drinks, fruit juice drinks, vegetable juices, sports drinks, isotonic drinks, enhanced waters, mineral waters, near waters, and energy drinks. Examples of the foods of the present invention may include functional foods, dietary supplements, foods with nutrient function claims, foods for special dietary uses, foods for specified health uses, nutritional supplements, foods for diet treatment, health foods, and supplements. Note that, the food or drink of the present invention may be prepared, for example, by mixing a cyclic dipeptide or a salt thereof in a predetermined amount with a raw material of a known food or drink, in accordance with a known production method for a food, or may be prepared by adding a cyclic dipeptide or a salt thereof to a known ready-made food or drink so as to satisfy the predetermined amount.

The composition according to the present invention can be applied to either one of therapeutic application (medical application) and non-therapeutic application (non-medical application). Specific examples thereof include use for drugs, quasi-drugs, and cosmetics, and include use for compositions which do not belong to drugs, quasi-drugs, or cosmetics under the Pharmaceutical Affairs Act but explicitly or implicitly claim an effect of ameliorating glucose metabolism, an effect of preventing diabetes, an effect of ameliorating diabetes, an effect of suppressing elevation of postprandial blood glucose level, an effect of suppressing appetite, an effect of preventing obesity or an effect of ameliorating obesity.

In another embodiment, the present invention relates to a composition provided with a label indicating a function developed by accelerating GLP-1 secretion. Examples of such an indication or functional indication include, but are not particularly limited to, "ameliorating glucose metabolism", "preventing diabetes", "ameliorating diabetes", "suppressing elevation of postprandial blood glucose level", "controlling blood glucose level", "suppressing appetite", "preventing obesity" or "ameliorating obesity". In the specification, a label of such indication or functional indication may be attached to the composition itself, or a container or package for the composition.

The composition according to the present invention can be ingested by an appropriate method in accordance with its dosage form. The ingestion method is not particularly limited as long as a cyclic dipeptide or a salt thereof and a sweetening agent contained in the composition according to the present invention can be transferred into circulating blood. Examples of the dosage form may include, but are not limited to, solid preparations for oral administration such as tablets, coated tablets, granules, powders, or capsules, liquid preparations for oral administration such as oral solutions or syrups, and preparations for parenteral administration such as injections, external preparations, suppositories, or transdermal preparations. In the specification, "ingestion" includes all dosage forms such as intake, administration, and drinking.

The application amount of the composition according to the present invention is not determined in a single uniform way and is appropriately determined in accordance with its dosage form, administration method, intended use, and the age, body weight, and symptoms of a patient or patient animal serving as an ingestion subject of the composition. The effective ingestion amount of the composition according to the present invention for a human in not determined in a single uniform way; and for example, the amount (by weight) per day of a cyclic dipeptide or a salt thereof according to the present invention to a human having a body weight of 50 kg, is preferably 0.1 mg or more and more preferably 1 mg or more. The amount (by weight) per day of a sweetening agent according to the present invention for a human having a body weight of 50 kg is preferably 0.1 mg or more, more preferably 1 mg or more, still more preferably 3 mg or more, and particularly preferably 30 mg or more. The dosage within a desired range of the amount of application may be administered once or the dosage is divided into several portions and administered the corresponding times per day. The administration period may be determined at discretion. Note that, herein, the effective ingestion amounts of a cyclic dipeptide or a salt thereof and sweetening agent per human according to the present invention mean the total ingestion amounts of the cyclic dipeptides or salts thereof and sweetening agents producing useful effects in a human. The types of cyclic dipeptide and sweetening agent are not particularly limited.

The subject to which the composition according to the present invention is to be applied is preferably a human; however, a domestic animal such as cattle, a horse and a goat, a pet animal such as a dog, a cat and a rabbit, or a laboratory animal such as a mouse, a rat, a guinea pig and a monkey, may be used. In the case of administration to animals except a human, the amount of use per day to a mouse individual (per approximately 20 g) varies depending on the conditions including the contents of a cyclic dipeptide or a salt thereof and a sweetening agent in a composition, and the condition, body weight, sex, and age of the subject to be administered. Usually, the total blending amount of cyclic dipeptides or salt thereof is set such that a subject can ingest preferably 0.1 mg/kg or more, and more preferably 1 mg/kg or more. The total blending mount of sweetening agents is set such that preferably 0.002 mg/kg or more, more preferably 0.02 mg/kg or more, still more preferably 3 mg/kg or more, and particularly preferably 30 mg/kg or more can be ingested.

5. Use of Composition Containing a Cyclic Dipeptide and a Sweetening Agent for Accelerating GLP-1 Secretion An embodiment of the present invention is use of a composition containing a cyclic dipeptide or a salt thereof and a sweetening agent, in which the content of the cyclic dipeptide or a salt thereof is $5.0 \times 10^{-4}$ ppm to $1.5 \times 10^4$ ppm and the content ratio of the cyclic dipeptide or a salt thereof and the sweetening agent falls within the range of 1:30 to 1:15000000, for accelerating GLP-1 secretion.

The cyclic dipeptide preferably includes either one or both of cyclo(glycyl-tyrosine) [Cyclo(Gly-Tyr)] and cyclo (leucyl-phenylalanine) [Cyclo(Leu-Phe)]. The sweetening agent preferably includes one or two or more members selected from the group consisting of glucose, sucralose, acesulfame potassium, aspartame and steviol glycoside. The steviol glycoside preferably includes one or two or more members selected from the group consisting of stevioside, rebaudioside A, rebaudioside B, rebaudioside C and rebaudioside D.

The type and content of a cyclic dipeptide or a salt thereof the type and content of a sweetening agent, the range of the content ratio of the cyclic dipeptide or a salt thereof and the sweetening agent and others are the same as described above about the composition. Specific examples of other additional components and amounts thereof are also the same as described above about the composition.

Examples of the use of the present invention include, but are not limited to, use for ameliorating glucose metabolism, suppressing appetite or preventing or meliorating diabetes or obesity. The use includes use for a human or a non-human animal, and may be therapeutic use or non-therapeutic use. The "non-therapeutic" use herein does not conceptually include a medical practice, that is, a therapeutic treatment for a human body.

6. Method for Accelerating GLP-1 Secretion

An embodiment of the present invention is a method for accelerating GLP-1 secretion by using a composition containing a cyclic dipeptide or a salt thereof and a sweetening agent, in which the content of the cyclic dipeptide or a salt thereof in the composition is $5.0 \times 10^{-4}$ ppm to $1.5 \times 10^4$ ppm, the content ratio of the cyclic dipeptide or a salt thereof and the sweetening agent falls within the range of 1:30 to 1:15000000.

The cyclic dipeptide preferably includes either one or both of cyclo(glycyl-tyrosine) [Cyclo(Gly-Tyr)] and cyclo(leucyl-phenylalanine) [Cyclo(Leu-Phe)]. The sweetening agent preferably includes one or two or more members selected from the group consisting of glucose, sucralose, acesulfame potassium, aspartame and steviol glycoside. The steviol glycoside preferably includes one or two or more members selected from the group consisting of stevioside, rebaudioside A, rebaudioside B, rebaudioside C and rebaudioside D.

The type and content of a cyclic dipeptide or a salt thereof the type and content of a sweetening agent, the range of the content ratio of the cyclic dipeptide or a salt thereof and the sweetening agent and others are the same as described above about the composition. Specific examples of other additional components and amounts thereof are also the same as described above about the composition.

In the method, a subject in which GLP-1 secretion needs to be accelerated is the same as the subject to which the composition according to the present invention is to be applied. In the specification, a therapeutically effective amount refers to the amount of the composition (according to the present invention) to be administered to a subject in which GLP-1 secretion is accelerated, compared to the subject not administered with the composition. The effective amount is not specifically determined in a single uniform way and appropriately determined in accordance with the dosage form, administration method, intended use, and the age, body weight, and symptoms of a subject.

In the method of the present invention, the specified cyclic dipeptide or a salt thereof or a sweetening agent may be administered as it is or a composition containing a specified cyclic dipeptide or a salt thereof or a sweetening agent may be administered so as to satisfy the treatment effective amount.

According to the method of the present invention, it is possible to accelerate secretion of GLP-1 without developing a side effect.

7. GLP-1 Secretion-Accelerating Composition

An embodiment of the present invention is a GLP-1 secretion-accelerating composition containing a specified steviol glycoside as an active ingredient.

In the specification, "steviol glycoside" is the same as defined above. In the GLP-1 secretion-accelerating composition according to the present invention, the steviol glycoside contained as an active ingredient is preferably one or two or more members selected from the group consisting of stevioside, RebA, RebB and RebD, and more preferably contains at least one of RebB and RebD.

In the GLP-1 secretion-accelerating composition according to the present invention, the content of steviol glycoside is not particularly limited as long as a desired effect of the present invention can be obtained in view of e.g., the dosage form and the administration method. For example, the total amount of steviol glycosides in the GLP-1 secretion-accelerating composition according to the present invention is 50 ppm or more, preferably 70 ppm or more and more preferably 100 ppm or more; $1.0 \times 10^5$ ppm or less, preferably $2.5 \times 10^4$ ppm or less and more preferably $1.0 \times 10^4$ ppm or less; and typically, 50 ppm to $1.0 \times 10^5$ ppm, preferably 70 ppm to $2.5 \times 10^4$ ppm, and more preferably 100 ppm to $1.0 \times 10^4$ ppm. In the GLP-1 secretion-accelerating composition according to the present invention, the total amount of steviosides is preferably 200 ppm to $5.0 \times 10^4$ ppm, preferably 400 ppm to $1.0 \times 10^4$ ppm, and more preferably 800 ppm to $5.0 \times 10^3$ ppm. In the GLP-1 secretion-accelerating composition according to the present invention, the amount of rebaudioside A is preferably 200 ppm to $5.0 \times 10^4$ ppm, preferably 400 ppm to $1.0 \times 10^4$ ppm and more preferably 800 ppm to $5.0 \times 10$ ppm. In the GLP-1 secretion-accelerating composition according to the present invention, the amount of rebaudioside B is preferably 200 ppm to $5.0 \times 10^4$ ppm, preferably 400 ppm to $1.0 \times 10^4$ ppm and more preferably 800 ppm to $5.0 \times 10^3$ ppm. In the GLP-1 secretion-accelerating composition according to the present invention, the amount of rebaudioside D is preferably 200 ppm to $5.0 \times 10^4$ ppm, preferably 400 ppm to $1.0 \times 10^4$ ppm and more preferably 800 ppm to $5.0 \times 10^3$ ppm.

The concentration of steviol glycoside blended in the composition according to the present invention can be measured by a known method such as HPLC.

The GLP-1 secretion-accelerating composition according to the present invention can contain any additives or components usually used, other than steviol glycoside, depending on the dosage form. Examples of these additives and/or components include, but are not limited to, physiologically active ingredients such as vitamins, minerals, nutrient components and fragrances; diluents, binders, emulsifiers, tonicity agents (isotonic agents), buffers, solubilizers, antiseptic agents, stabilizers, antioxidants, colorants, coagulants, and coating agents to be blended in formulating a preparation.

The GLP-1 secretion-accelerating composition according to the present invention has a feature of containing an effectiveness amount of steviol glycoside mentioned above. Owing to this, secretion of GLP-1 is accelerated and thus, e.g., an effect of ameliorating glucose metabolism and an effect of suppressing appetite can be exerted. As a result, an effect of treating, preventing or ameliorating diabetes or obesity, or an effect of treating, preventing or ameliorating diabetes related diseases is produced. Accordingly, an embodiment of the present invention is a GLP-1 secretion-accelerating composition containing a specified steviol glycoside as an active ingredient, more specifically, the composition having action to ameliorate glucose metabolism, an action to suppress appetite and an action to treatment, prevention or ameliorate diabetes or obesity.

Examples of the GLP-1 secretion-accelerating composition according to the present invention include, but are not limited to, drugs, drinks, foods and cosmetics. Specific examples of the drinks and foods are the same as mentioned above. Note that, the food or drink of the present invention may be prepared, for example, by mixing a steviol glycoside as mentioned above in a predetermined amount with a raw material of a known food or drink in accordance with a known production method for foods, or may be prepared by adding a steviol glycoside as mentioned above to a known ready-made food or drink so as to satisfy the predetermined amount.

The GLP-1 secretion-accelerating composition according to the present invention can be applied to either one of therapeutic application (medical application) and non-therapeutic application (non-medical application). Specific examples thereof include use for drugs, quasi-drugs, and cosmetics, and include use for compositions which do not belong to drugs, quasi-drugs or cosmetics under the Pharmaceutical Affairs Act and nevertheless explicitly or implicitly claim an effect of ameliorating glucose metabolism, an effect of preventing diabetes, an effect of ameliorating diabetes, an effect of suppressing an elevation of postprandial blood glucose level, an effect of suppressing appetite, an effect of preventing obesity and an effect of ameliorating obesity.

In another embodiment, the present invention relates to the composition provided with a label indicating a function developed by accelerating a GLP-1 secretion. Examples of such an indication or functional indication include, but are not particularly limited to, "ameliorating glucose metabolism", "preventing diabetes", "ameliorating diabetes", "suppressing elevation of postprandial blood glucose level", "controlling blood glucose level", "suppressing appetite", "preventing obesity" and "ameliorating obesity". In the specification, a label of indication or functional indication may be attached to the composition itself or a container or package for the composition.

The GLP-1 secretion-accelerating composition according to the present invention can be ingested by using an appropriate method in accordance with its dosage form. The ingestion method is not particularly limited as long as a cyclic dipeptide or a salt thereof and a sweetening agent contained in the composition according to the present invention can be transferred into circulating blood. Examples of the dosage form may include, but are not limited to, solid preparations for oral administration such as tablets, coated tablets, granules, powders, or capsules, liquid preparations for oral administration such as oral solutions or syrups, and preparations for parenteral administration such as injections, external preparations, suppositories, or transdermal preparations. In the specification, "ingestion" includes all dosage forms such as intake, administration, and drinking.

The application amount of the GLP-1 secretion-accelerating composition according to the present invention is not determined in a single uniform way and is appropriately determined in accordance with its dosage form, administration method, intended use, and the age, body weight and symptoms of a patient or patient animal serving as an indigestion subject of the composition. The effective ingestion amount of the composition according to the present invention for a human is not determined in a single uniform way; and for example, the amount (by weight) per day of a steviol glycoside according to the present invention to a human with a body weight of 50 kg, is preferably 0.1 mg or more and more preferably 1 mg or more. The dosage within a desired range of the amount of application may be administered once or the dosage is divided into several portions and administered the corresponding times per day. The administration period may be determined at discretion. Note that, herein, the effective ingestion amount of a steviol glycoside per human according to the present invention refers to the sum of the ingestion amounts of steviol glycosides which provide useful effects in a human.

The subject to which the GLP-1 secretion-accelerating composition according to the present invention is to be applied is preferably a human; however, a domestic animal such as cattle, a horse, and a goat, a pet animal such as a dog, a cat, and a rabbit, or a laboratory animal such as a mouse, a rat, a guinea pig, and a monkey may be used. In the case of administration to animals except a human, the amount of use per day to a mouse individual (per approximately 20 g) varies depending on the conditions including the content of a steviol glycoside in a composition, and the condition, body weight, sex, and age of the subject to be administered, and usually, the total blending amount of steviol glycosides may be set so as to administer 0.002 mg/kg or more, more preferably 0.02 mg/kg or more.

8. Use of Steviol Glycoside for Accelerating GLP-1 Secretion

An embodiment of the present invention is use of a steviol glycoside for accelerating GLP-1 secretion. As the steviol glycoside to be used as an active ingredient, one or two or more members selected from the group consisting of stevioside, RebA, RebB and RebD are included; and more preferably, at least one of RebB and RebD is included.

The type and content of a steviol glycoside are the same as described above. Specific examples of other additional components and amounts thereof are also the same as described above.

Examples of the use according to the present invention include, but are not limited to, use for amelioration of glucose metabolism, appetite suppression or prevention or amelioration of diabetes or obesity. The use includes use for a human or a (non-human) animal, and may be therapeutic use or non-therapeutic use. The "non-therapeutic" use herein does not conceptually include a medical practice, that is, a treatment practice for a human body by therapy.

9. Method for Accelerating GLP-1 Secretion

An embodiment of the present invention is to provide a method for accelerating GLP-1 secretion, including administering a therapeutically effective amount of a specified steviol glycoside as an active ingredient to a subject required for accelerating GLP-1 secretion. In the method, as the steviol glycoside to be used as an active ingredient, one or two or more members selected from the group consisting of stevioside, RebA, RebB and RebD are included; and more preferably, at least one of RebB and RebD is included.

Note that, the subject required for accelerating GLP-1 secretion is the same as the subject to which the GLP-1 secretion-accelerating composition according to the present invention is to be applied.

In the specification, a therapeutically effective amount refers to the amount of the steviol glycoside according to the present invention for increasing GLP-1 secretion in a subject to which the steviol glycoside is allowed to ingest, compared to the subject to which the steviol glycoside is not allowed to ingest. The effective amount is not specifically determined in a single uniform way and appropriately determined in accordance with the dosage form, administration method, intended use, and the age, body weight, and symptoms of a subject.

In the method of the present invention, the specified steviol glycoside may be administered as it is or a composition containing a steviol glycoside may be administered.

According to the method of the present invention, it is possible to accelerate secretion of GLP-1 without developing a side effect.

EXAMPLES

Now, the present invention will be more specifically described with reference to Examples, which will not limit the scope of the present invention. The method according to the present invention will be varied and modified in various ways by those skilled in the art and such modifications and variations are also included in the scope of the present invention.

Example 1. Effect of Cyclic Dipeptide on Enhancement of a GLP-1 Secretion-Accelerating Action of Sweetening Agent (1-1) Reagents As cyclic dipeptides: cyclo(glycyl-tyrosine) [Cyclo(Gly-Tyr)] (CGY) and cyclo(leucyl-phenylalanine) [Cyclo(Leu-Phe)] (CLF), and chemical synthesized preparations were used. Poly-L-Lysine 96-well plates were obtained from Becton Dickinson (BD). PBS (+), an antibiotic substance, Dulbecco's Modified Eagle's Medium (DMEM) and glucose used herein were obtained from Nacalai Tesque Inc.; sucralose, acesulfame potassium and aspartame from Wako Pure Chemical Industries Ltd.; active GLP-1 ELISA kit from Merck Millipore, Fetal bovine serum (FBS) from Sigma; and Sitagliptin phosphate from SantaCruz Biotechnology. Human intestinal cell strain, NCI-H716 cells used herein were provided by ATCC.

(1-2) Analysis

In the following test examples, data were each shown by an average value±a standard error.

(1-3) Cell Culture

NCI-H716 cells, which were suspended in DMEM culture medium (containing 10% FBS, 2 mM glutamine, 1% antibiotic substance), were seeded in Poly-L-Lysine 96-well plates in an amount of 100 μL for each so as to contain $0.5 \times 10^5$ cells/well and cultured in a $CO_2$ incubator (manufactured by ESPEC CORP.) for 48 hours.

(1-4) Preparation of Reaction Solution

Sweetening agent solutions were prepared each by adding a sweetening agent to PBS (+). In the case of glucose, a concentration was set at 3%, sucralose at 0.6%, acesulfame potassium at 0.3%, and aspartame at 0.3%. A cyclic dipeptide was dissolved in DMSO and then added to each of sweetening agent solutions so as to obtain final concentrations shown in Table 1 and Table 2. Note that, all cell addition solutions were prepared such that DMSO (0.1%) and a 10 μM Sitagliptin phosphate were contained.

(1-5) Addition to Cell, Recovery, Quantification of GLP-1

After the cells were washed once with PBS (+), a reaction solution was added to the cells. One hour later, the solution added was recovered. Thereafter, the amount of active GLP-1 in the solution recovered was measured by using the ELISA kit. Analysis was carried out using relative values to the amount of active GLP-1 (regarded as 100) in a (sample) group to which neither sweetening agent nor cyclic dipeptide were added.

The results are shown in Tables 1 and 2.

TABLE 1

| Sample | | Average value | Standard error |
|---|---|---|---|
| Control | | 100 | 11 |
| Glucose (3%) | | 129 | 6 |
| | +CGY (0.000001%) | 154 | 7 |
| | +CGY (0.0001%) | 149 | 8 |
| Sucralose (0.6%) | | 206 | 12 |
| | +CGY (0.00001%) | 224 | 10 |
| | +CGY (0.001%) | 235 | 20 |
| Acesulfame K (0.3%) | | 125 | 9 |
| | +CGY (0.00001%) | 154 | 9 |
| | +CGY (0.001%) | 163 | 17 |
| Aspartame (0.3%) | | 112 | 13 |
| | +CGY (0.00001%) | 144 | 7 |
| | +CGY (0.001%) | 154 | 9 |

TABLE 2

| Sample | | Average value | Standard error |
|---|---|---|---|
| Control | | 100 | 8 |
| Glucose (3%) | | 183 | 11 |
| | +CLF (0.000002%) | 212 | 4 |
| | +CLF (0.0002%) | 226 | 11 |
| Sucralose (0.6%) | | 233 | 31 |
| | +CLF (0.00002%) | 287 | 19 |
| | +CLF (0.002%) | 282 | 14 |
| Acesulfame K (0.3%) | | 145 | 6 |
| | +CLF (0.00002%) | 168 | 9 |
| | +CLF (0.002%) | 184 | 13 |
| Aspartame (0.3%) | | 129 | 13 |
| | +CLF (0.00002%) | 168 | 2 |
| | +CLF (0.002%) | 214 | 9 |

As shown in Tables 1 and 2, it was found that in all cases of sweetening agents of glucose, sucralose, acesulfame potassium and aspartame, GLP-1 secretion amount increases in a cyclic dipeptide (Cyclo(Gly-Tyr) or Cyclo(Leu-Phe)) concentration-dependent manner.

Example 2: GLP-1 Secretion-Accelerating Action by a Combination of Stevioside or RebA and Cyclo(Leu-Phe)

As the reagents and others, those manufactured by the same manufacturers as described in Example 1 were used. In the following test examples, data were each shown by an average value±a standard error. As the statistical test, Excel Student's t-test was used. In the results, "*" represents a significant difference of <0.05, and "#" represents significant difference of p<0.1.

NCI-H716 cells, which were suspended in DMEM culture medium (containing 10% FBS, 2 mM glutamine, 1% antibiotic substance) were seeded in Poly-L-Lysine 96-well plates in an amount of 100 μL for each so as to contain $0.5 \times 10^5$ cells/well and cultured in an $CO_2$ incubator (manufactured by ESPEC CORP.) for 48 hours. After the cells were washed with PBS (+), a PBS (+) solution already containing 10 μM Sitagliptin phosphate was controlled such that the final concentration of stevioside or RebA was 0.01%, and the final concentration of Cyclo(Leu-Phe) was 0.02 μg/mL or 2 μg/mL. The PBS (+) solution (100 μL) was individually added to the NCI-H716 cells. One hour later, the solution added was recovered and the amount of active GLP-1 in the solution was measured by the ELISA kit. Analysis was carried out based on relative values to the amount of active GLP-1 (regarded as 100) in a (sample) group to which neither a steviol glycoside not Cyclo(Leu-Phe) were added The results are shown in Table 3 and FIG. 1. Note that, in FIG. 1, stevioside is represented by "Stev." and Cyclo(Leu-Phe) by "CLF". The sample) group containing Cyclo(Leu-Phe) in a final concentration of 0.02 μg/mL is represented by "CLF(Low)" and the (sample) group containing Cyclo(Leu-Phe) in a final concentration of 2 μg/mL is represented by "CLF(High)".

TABLE 3

|  |  | Control | Cyclo (Leu-Phe): 0.02 µg/mL | Cyclo (Leu-Phe): 2 µg/mL | Stevioside: 0.01% | Stevioside: 0.01% + Cyclo (Leu-Phe): 0.02 µg/mL | Stevioside: 0.01% + Cyclo (Leu-Phe): 2 µg/mL | RebA: 0.01% | RebA: 0.01% + Cyclo (Leu-Phe): 0.02 µg/mL | RebA: 0.01% + Cyclo (Leu-Phe): 2 µg/mL |
|---|---|---|---|---|---|---|---|---|---|---|
| Amount of Active GLP-1 (relative amount to control as 100) | Average value | 100.0 | 65.1 | 59.9 | 62.7 | 116.6 | 1238.7 | 72.6 | 143.2 | 133.5 |
|  | Standard error | 8.4 | 7.3 | 7.1 | 9.2 | 4.7 | 218.8 | 11.9 | 5.7 | 10.9 |

Figure 1:
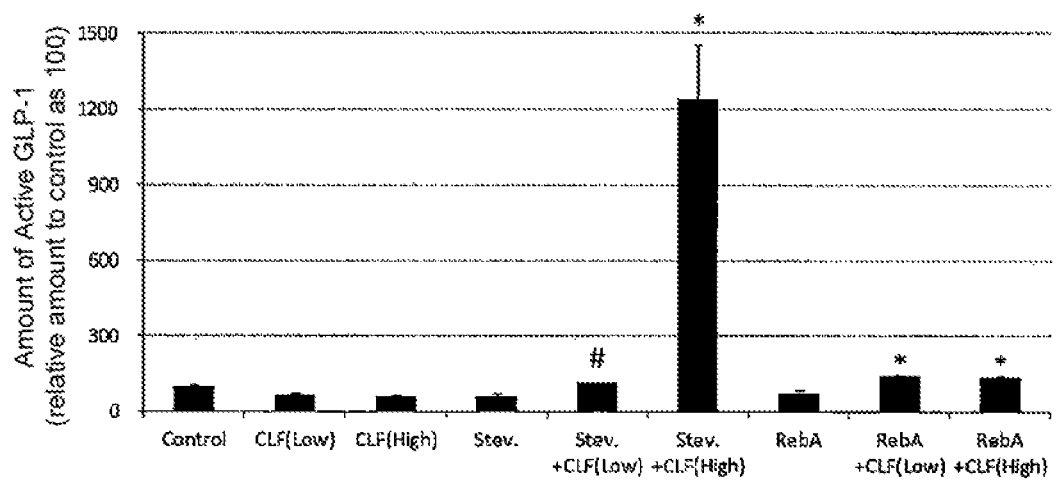
FIG. 1 is a graph showing the effects of stevioside+Cyclo (Len-Phe) and rebaudioside A+Cyclo(Leu-Phe) on GLP-1 secretion amount when NCI-H716 cells are cultured for one hour in the presence of each of them.

As shown in Table 3 and FIG. 1, it was found that GLP-1 secretion is not accelerated by either one of stevioside and RebA at a concentration of 0.01%; however, a GLP-1 secretion-accelerating action was obtained by using each of stevioside and RebA (0.01%) in combination with Cyclo (Leu-Phe).

Example 3: GLP-1 Secretion-Accelerating Action by Combination of RebD and Cyclo(Gly-Tyr)

The experiment was carried out in accordance with Example 2. A PBS (+) solution already containing 10 µM Sitagliptin phosphate was controlled such that the final concentration of RebD was 0.01%, and the final concentration of Cyclo(Gly-Tyr) was 0.01 µg/mL or 1 µg/mL. The PBS (+) solution (100 µL) was individually added to the NCI-H716 cells. After that, the measurement and statistical analysis of active GLP-1 amount were carried out in the same manner as in Example 2.

The results are shown in Table 4 and FIG. 2. Note that, in FIG. 2. Cyclo(Gly-Tyr) is represented by "CGY". The (sample) group containing Cyclo(Gly-Tyr) in a final concentration of 0.01 µg/mL is represented by "CLF(Low)" and the (sample) group containing Cyclo(Gly-Tyr) in a final concentration of 1 µg/mL is represented by "CLF(High)".

TABLE 4

|  |  | Control | Cyclo (Gly-Tyr): 0.01 µg/mL | Cyclo (Leu-Phe): 1 µg/mL | Stevioside: 0.01% | Stevioside: 0.01% + Cyclo (Gly-Tyr): 0.01 µg/mL | Stevioside: 0.01% + Cyclo (Gly-Tyr): 1 µg/mL | RebA: 0.01% | RebA: 0.01% + Cyclo (Gly-Tyr): 0.01 µg/mL | RebA: 0.01% + Cyclo (Gly-Tyr): 1 µg/mL |
|---|---|---|---|---|---|---|---|---|---|---|
| Amount of Active GLP-1 (relative amount to control as 100) | Average value | 100.0 | 65.1 | 59.9 | 62.7 | 116.6 | 1238.7 | 72.6 | 143.2 | 133.5 |
|  | Standard error | 8.4 | 7.3 | 7.1 | 9.2 | 4.7 | 218.8 | 11.9 | 5.7 | 10.9 |

As shown in Table 4 and FIG. 2, it was found that GLP-1 secretion is not accelerated by RebD alone at a concentration of 0.01%; however, a GLP-1 secretion-accelerating action was obtained by using RebD (0.01%) in combination with Cyclo(Gly-Tyr).

Example 4: GLP-1 Secretion-Accelerating Action by Steviol Glycoside

NCI-H716 cells, which were suspended in DMEM culture medium (containing 10% FBS, 2 mM glutamine, 1% antibiotic substance), were seeded in Poly-L-Lysine 96-well plates in an amount of 100 µL for each so as to add $0.5 \times 10^5$ cells/well and cultured in an $CO_2$ incubator (manufactured by ESPEC CORP.) for 48 hours. After the cells were washed with PBS (+), a PBS (+) solution already containing 10 µM Sitagliptin phosphate was controlled such that the final concentration of stevioside, RebA or RebB was 0.001, 0.01 or 0.1%. The PBS (+) solution (100 µL) controlled such that the final concentration of RebC or RebD was 0.001 or 0.01% was added to the cells. One hour later, the solution added was recovered and the amount of active GLP-1 in the solution was measured by the ELISA kit. Analysis was carried out based on relative values to the amount of active GLP-1 (regarded as 100) in a (sample) group to which a steviol glycoside was not added.

The results are shown in Table 5 and FIG. 3.

TABLE 5

|  |  | Control | TPA | Stevioside 0.001% | Stevioside 0.01% | Stevioside 0.1% | RebA 0.001% | RebA 0.01% | RebA 0.1% |
|---|---|---|---|---|---|---|---|---|---|
| Amount of Active GLP-1 (relative amount to control as 100) | Average value | 100.0 | 131.7 | 104.9 | 91.3 | 160.9 | 92.8 | 129.3 | 150.9 |
|  | Standard error | 15.6 | 10.6 | 7.6 | 5.2 | 21.6 | 12.0 | 15.0 | 20.6 |

|  |  | Contrl | RebB 0.001% | RebB 0.01% | RebB 0.1% | RebC 0.001% | RebC 0.01% | RebD 0.001% | RebD 0.01% |
|---|---|---|---|---|---|---|---|---|---|
| Amount of Active GLP-1 (relative amount to control as 100) | Average value | 100.0 | 82.0 | 70.5 | 151.2 | 52.8 | 55.0 | 63.1 | 170.0 |
|  | Standard error | 31.2 | 13.0 | 8.3 | 30.0 | 11.2 | 8.5 | 8.3 | 22.3 |

As shown in Table 5 and FIG. 3, it was found that a GLP-1 secretion-accelerating action was not observed in RebC; however, a GLP-1 secretion-accelerating action can be obtained by adding stevioside, RebA, RebB and RebD.

INDUSTRIAL APPLICABILITY

The present invention relates to a composition containing a cyclic dipeptide or a salt thereof and a sweetening agent in a specified ratio. Owing to this, GLP-1 secretion-accelerating effect derived from a single sweetening agent can be enhanced. The cyclic dipeptide contained in the composition according to the present invention is contained in a heat-treated material of plant-derived peptides and thus high in safety. A risk of developing a serious side effect for the composition according to the present invention is extremely low. The present invention also provides e.g., a GLP-1 secretion-accelerating composition containing a specified steviol glycoside as an active ingredient. Accordingly, the present invention provides a novel means contributing to amelioration of glucose metabolism or prevention or amelioration of diabetes or obesity and thus has industrially high applicability.

The invention claimed is:

1. A composition containing a cyclic dipeptide or a salt thereof and a sweetening agent, wherein
the content of the cyclic dipeptide or a salt thereof in the composition is $5.0 \times 10^{-4}$ ppm to $1.5 \times 10^4$ ppm, wherein the cyclic dipeptide includes cyclo(glycyl-tyrosine) [Cyclo(Gly-Tyr)] and cyclo(leucyl-phenylalanine) [Cyclo(Leu-Phe)]; and
wherein the sweetening agent comprises one or two or more members selected from the group consisting of sucralose, acesulfame potassium, and aspartame;
when the sweetening agent includes sucralose, the content ratio of the cyclic dipeptide or a salt thereof and sucralose is 1:300 to 1:60000;
when the sweetening agent includes acesulfame potassium, the content ratio of the cyclic dipeptide or a salt thereof and acesulfame potassium is 1:150 to 1:30000; and
when the sweetening agent contains aspartame, the content ratio of the cyclic dipeptide or a salt thereof and aspartame is 1:150 to 1:30000.

2. The composition according to claim 1, further comprising
glucose, and
the content ratio of the cyclic dipeptide or a salt thereof and glucose is 1:3000 to 1:15000000.

3. The composition according to claim 1, wherein
the sweetening agent includes sucralose, and
the content ratio of the cyclic dipeptide or a salt thereof and sucralose is 1:300 to 1:60000.

4. The composition according to claim 1, wherein
the sweetening agent includes acesulfame potassium, the content ratio of the cyclic dipeptide or a salt thereof and acesulfame potassium is 1:150 to 1:30000.

5. The composition according to claim 1, wherein
the sweetening agent contains aspartame, and
the content ratio of the cyclic dipeptide or a salt thereof and aspartame is 1:150 to 1:30000.

6. The composition according to claim 1, wherein the content of the sweetening agent is 1.0 ppm to $6.0 \times 10^5$ ppm.

7. The composition according to claim 1, wherein the content of the sweetening agent is 0.5 wt % to 600 wt % in terms of sucrose concentration.

8. The composition according to claim 1, wherein the cyclic dipeptide or a salt thereof is obtained from a soybean peptide, a tea peptide or a malt peptide.

9. The composition according to claim 1, having a GLP-1 secretion-accelerating action.

10. The composition according to claim 1, for ameliorating glucose metabolism, suppressing appetite or preventing or ameliorating diabetes or obesity.

11. A method for accelerating secretion of GLP-1 by administering a composition of claim 1 to a subject.

* * * * *